US010143864B2

(12) United States Patent
Mittelstadt

(10) Patent No.: US 10,143,864 B2
(45) Date of Patent: Dec. 4, 2018

(54) RESPIRATOR HAVING NONCIRCULAR CENTROID-MOUNTED EXHALATION VALVE

(71) Applicant: 3M INNOVATIVE PROPERTIES COMPANY, St. Paul, MN (US)

(72) Inventor: William A. Mittelstadt, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 802 days.

(21) Appl. No.: 14/538,117

(22) Filed: Nov. 11, 2014

(65) Prior Publication Data
US 2015/0136141 A1 May 21, 2015

Related U.S. Application Data

(60) Provisional application No. 61/904,859, filed on Nov. 15, 2013.

(51) Int. Cl.
| *A61M 16/20* | (2006.01) |
| *A62B 18/10* | (2006.01) |
| *F16K 15/14* | (2006.01) |
| *A62B 18/02* | (2006.01) |
| *A62B 23/02* | (2006.01) |

(52) U.S. Cl.
CPC .............. *A62B 18/10* (2013.01); *A62B 18/02* (2013.01); *A62B 18/025* (2013.01); *A62B 23/025* (2013.01); *F16K 15/148* (2013.01); *A61M 2205/15* (2013.01); *A61M 2205/75* (2013.01); *Y10T 137/7891* (2015.04)

(58) Field of Classification Search
CPC ....... A62B 18/02; A62B 18/025; A62B 18/10; A61M 16/208; A61M 16/209; F16K 15/14; F16K 15/148
See application file for complete search history.

(56) References Cited

U.S. PATENT DOCUMENTS

| 2,072,516 A | 3/1937 | Ferenci |
| 2,230,770 A | 2/1941 | Almelo |
| (Continued) |

FOREIGN PATENT DOCUMENTS

| DE | 4327531 | 2/1995 |
| GB | 1517090 | 7/1978 |
| (Continued) |

OTHER PUBLICATIONS

International Application PCT/US2014/064919 Search Report dated Feb. 24, 2015.

*Primary Examiner* — Lynne Anderson

(57) ABSTRACT

A respirator 10 that has a mask body 12 and a harness 16 has an exhalation valve 23 that includes a valve seat 36 and a flexible flap 42. The valve seat 36 has an orifice 38 and has a noncircular seal surface 40 surrounding the orifice 38. The flexible flap 42 is secured to the valve seat 36 at a centroid of the orifice and has a variable stiffness structure. The variable stiffness structure allows the flap to equally deflect under a given load at different distances from the centroid at the noncircular seal surface. An exhalation valve having this construction may beneficially optimize pressure drop and overall valve performance for applications where valve space may be limited.

18 Claims, 4 Drawing Sheets

(56) References Cited

U.S. PATENT DOCUMENTS

| | | | |
|---|---|---|---|
| 2,895,472 A | 7/1959 | Matheson | |
| 3,085,591 A * | 4/1963 | Schneider | A62B 18/10 137/854 |
| 3,474,783 A * | 10/1969 | Ulmann | A62B 18/10 128/206.15 |
| 4,191,211 A | 3/1980 | Walker | |
| 4,565,214 A | 1/1986 | Parman | |
| 4,630,604 A | 12/1986 | Montesi | |
| 4,790,306 A | 12/1988 | Braun | |
| 4,850,346 A | 7/1989 | Michel | |
| 4,934,362 A | 6/1990 | Braun | |
| 5,062,421 A | 11/1991 | Burns | |
| 5,325,892 A | 7/1994 | Japuntich | |
| 5,509,436 A | 4/1996 | Japuntich | |
| 5,687,767 A | 11/1997 | Bowers | |
| 5,937,850 A | 8/1999 | Kawashima | |
| 6,047,698 A | 4/2000 | Magidson | |
| 6,070,574 A * | 6/2000 | O'Day | A61M 16/107 128/202.28 |
| 6,176,239 B1 * | 1/2001 | Grove | A62B 18/02 128/201.15 |
| 6,412,514 B1 | 7/2002 | Raftis | |
| 6,732,733 B1 | 5/2004 | Brostrom | |
| 6,715,490 B2 | 11/2004 | Byram | |
| 6,883,518 B2 | 4/2005 | Mittelstadt | |
| 6,923,182 B2 | 8/2005 | Angadjivand | |
| 7,013,895 B2 | 3/2006 | Martin | |
| 7,028,689 B2 | 4/2006 | Martin | |
| 7,128,070 B2 * | 10/2006 | Wiener | A62B 18/02 128/201.15 |
| 7,131,442 B1 | 11/2006 | Kronzer | |
| 7,188,622 B2 | 3/2007 | Martin | |
| 7,252,110 B2 | 8/2007 | Semeia | |
| 7,302,951 B2 | 12/2007 | Mittelstadt | |
| 7,493,900 B1 | 2/2009 | Japuntich | |
| 7,650,884 B2 | 1/2010 | Flannigan | |
| 8,777,036 B2 * | 7/2014 | Malec | B60K 15/077 220/4.12 |
| 2002/0195108 A1 | 12/2002 | Mittelstadt | |
| 2009/0078264 A1 | 3/2009 | Martin | |
| 2009/0133700 A1 | 5/2009 | Martin | |
| 2012/0167890 A1 | 7/2012 | Insley | |
| 2012/0168658 A1 | 7/2012 | Insley | |
| 2013/0068232 A1 | 3/2013 | Rosert | |
| 2013/0125896 A1 | 5/2013 | Dwyer | |

FOREIGN PATENT DOCUMENTS

| | | |
|---|---|---|
| JP | 2006-122146 | 5/2006 |
| RU | 2120531 | 10/1998 |

* cited by examiner

RESPIRATOR HAVING NONCIRCULAR CENTROID-MOUNTED EXHALATION VALVE

The present invention pertains to a respirator where the exhalation valve has a non-circular, centroid-mounted flexible flap.

BACKGROUND

Persons who work in polluted environments commonly wear respirators to protect themselves from inhaling airborne contaminants. Respirators typically have a fibrous or sorbent filter that is capable of removing particulate and/or gaseous contaminants from the air. When wearing a respirator in a contaminated environment, wearers are comforted with the knowledge that their health is being protected, but they are, however, contemporaneously discomforted by the warm, moist, exhaled air that accumulates around their face. The greater this facial discomfort is, the greater chances are that the wearer may remove the respirator from their face to alleviate the unpleasant condition. To reduce the likelihood of this occurrence, respirator manufacturers often install an exhalation valve on the mask body to allow the warm, moist, exhaled air to be rapidly purged from the mask interior. The rapid removal of the exhaled air makes the mask interior cooler, which, in turn, benefits worker safety.

For many years, commercial respiratory masks have used "button-style" exhalation valves to purge exhaled air from mask interiors. The button-style valves typically have employed a thin, circular, flexible flap as the dynamic mechanical element that lets exhaled air escape from the interior gas space. The circular flap has been centrally-mounted to a valve seat through a central post. Examples of button-style valves are shown in U.S. Pat. Nos. 2,072,516, 2,230,770, 2,895,472, and 4,630,604. When a person exhales, a circumferential portion of the flap is lifted from the valve seat so that the air can rapidly pass from the interior gas space into the exterior gas space.

Button-style valves have represented an advance in the attempt to improve wearer comfort, but investigators have made other improvements, an example of which is the "butterfly-style" valve shown in U.S. Pat. No. 4,934,362 to Braun. The valve described in the Braun patent uses a parabolic valve seat and an elongated flexible flap mounted in butterfly fashion.

After the Braun development, another innovation was made in the exhalation valve art by Japuntich et al.—see U.S. Pat. Nos. 5,325,892 and 5,509,436. The Japuntich et al. valve used a single flexible flap that is mounted off-center in cantilevered fashion to minimize the exhalation pressure that is required to open the valve. When the valve-opening pressure is minimized, less power is required to operate the valve, which means that the wearer does not need to work as hard to expel exhaled air from the mask interior when breathing—see also, U.S. Pat. No. 7,493,900 to Japuntich et al.

Other valves that have been introduced after the Japuntich et al. valve also have used cantilevered mounted flaps—see U.S. Pat. Nos. 5,687,767 and 6,047,698. In yet another development, the seal surface of the valve seat has been made from a resilient material that allows a thinner, yet stiffer flap to be used, which improves the valve efficiency—see U.S. Pat. No. 7,188,622 to Martin et al.

Although the evolution of exhalation valve design has centered mainly around structural changes relative to the valve seat and the mounting of the flap to it, investigators also have made structural changes to the flap itself to enhance valve performance. In U.S. Pat. Nos. 7,028,689 and 7,013,895 to Martin et al., multiple layers were introduced into the flap to create a thinner, more dynamic flap, which allowed the valve to open easier under less pressure. Ribs and a pre-curved, non-uniform, configuration also have been provided in the flap construction to provide good performance—see U.S. Pat. No. 7,302,951 to Mittelstadt et al. In U.S Patent Publication No. 2009/0133700 to Martin et al., slots have been provided in the valve flap at the hinge to improve valve performance. Also, in U.S. Published Application 2012/0167890A to Insley et al., the flap was ablated in selected areas to achieve desired valve performance. Flaps also have been made of an optical film, which causes the flap to flash so that users can readily detect proper valve operation—see U.S. Patent Application 61/846,456 to Martin et al.

Respirator designs come in a variety of shapes and configurations and the design is often influenced by the orientation and placement of the filter cartridges and any exhalation valve that is placed on the mask body. Cantilevered valves, for example, are commonly oriented vertically on the mask body, with the free end of the flap pointed downward. If oriented otherwise, the exhaled air may have the opportunity to fog a user's eyewear. Valve designs for high performance exhalation valves therefore can place constraints on mask body design. A new valve that can deliver exceptional valve performance, like a cantilevered valve, without having to be oriented vertically can help to alleviate constraints in valve design. The present invention described below has been created to provide such a valve.

SUMMARY OF THE INVENTION

The present invention provides an exhalation valve that comprises:
(a) a valve seat that has an orifice and that has a noncircular seal surface surrounding the orifice; and
(b) a flexible flap that is secured to the valve seat at a centroid of the orifice and that has a variable stiffness structure.

The present invention also provides a respirator that comprises:
(a) a harness; and
(b) a mask body that comprises an exhalation valve that includes:
  (i) a valve seat that has an orifice and that has a noncircular seal surface surrounding the orifice; and
  (ii) a flexible flap that is secured to the valve seat at a centroid of the orifice and that has a variable stiffness structure.

The present invention differs from known exhalation valves in that the inventive valve has a variable stiffness structure that allows the flap of a noncircular, centrally-mounted valve to be equally deflected at essentially any point along the flap perimeter. The ability to so equally deflect enables the valve to open freely and easily from the whole flap perimeter—that is, essentially the same force will lift the flap from the valve seat at any point around the perimeter. The variable stiffness structure can be fashioned to keep the valve closed under any orientation when the user is not exhaling, while, at the same time, provide the minimal force needed to open the valve during an exhalation. Reductions in exhalation pressure increase wearer comfort, particularly when the wearer is undergoing a strenuous activity. And, as indicated above, lower exhalation pressure improves wearer safety by reducing the likelihood that the wearer will displace the respirator from their face during use. The invention therefore can enhance worker safety while also allowing the valve and respirator to be fashioned into a variety of shapes and configurations. The valve can be mounted on the mask body in a variety of orientations. The present invention therefore can expand the design window for exhalation valves and respirators, with the added benefit of providing exceptional performance needed by respirator wearers.

Glossary

The terms set forth below will have the meanings as defined:

"alignment element" means a part that assists in ensuring that a device to which the part is associated with is always in proper orientation during use;

"clean air" means a volume of atmospheric ambient air that has been filtered to remove contaminants;

"centroid" means the center of mass with or without the variable stiffness structure;

"comprises (or comprising)" means its definition as is standard in patent terminology, being an open-ended term that is generally synonymous with "includes", "having", or "containing" Although "comprises", "includes", "having", and "containing" and variations thereof are commonly-used, open-ended terms, this invention also may be suitably described using narrower terms such as "consists essentially of", which is semi open-ended term in that it excludes only those things or elements that would have a deleterious effect on the performance of the subject matter to which the term pertains;

"equally deflect" means that the ratio of the force exerted to cause the flexible flap to deflect at the location with the higher load to the force needed to cause the flap to deflect at the location with the lower load ("flap deflection ratio" or FDR), when tested according to the Flap Deflection Test set forth below, is less than 2;

"exhalation valve" means a valve that opens to allow exhaled air to exit the interior gas space of a respirator;

"exhaled air" means air that is exhaled by a respirator wearer;

"exterior gas space" means the ambient atmospheric gas space into which exhaled gas enters after passing through and beyond the mask body and/or exhalation valve;

"filter" or "filtration layer" means one or more layers of material, which layer(s) is adapted for the primary purpose of removing contaminants (such as particles) from an air stream that passes through it;

"filter media" means an air-permeable structure that is designed to remove contaminants from air that passes through it;

"flexible flap" means an article that can bend or flex in response to a force exerted from a person's exhale air stream;

"harness" means a structure or combination of parts that assists in supporting the mask body on a wearer's face;

"interior gas space" means the space between a mask body and a person's face;

"mask body" means a structure that can fit at least over the nose and mouth of a person and that helps define an interior gas space separated from an exterior gas space;

"major surface" means a surface that has a substantially larger surface area than other surfaces (but not all surfaces) in the article or body;

"noncircular" means not having the shape of a circle from viewed through a plane projected frontally onto the valve seat;

"orifice" means an opening, which may or may not be subdivided, sized to permit exhaled air to easily pass therethrough;

"outer surface" with respect to the flexible flap means the major surface that faces away from the seal surface when the flap is seated or resting on the valve seat;

"perimeter" with reference to the flexible flap means at or near the flap edge, typically within 3 millimeters (mm) of the flap edge;

"plurality" means two or more;

"respirator" means a device that is worn by a person to provide clean air for the wearer to breathe;

"seal surface" means the surface onto which the flexible flap rests when the valve is in a closed position;

"secured" means attached to in any fashion;

"slight bias" means the minimal bias needed to keep the flexible flap in a closed position, under any orientation, with no forces being exerted on the flap other than gravity.

"surrounding" means being located about the object in question from all directions;

"valve seat" or "valve base" means the solid part of a valve which has an orifice for a fluid to pass through it and which is disposed adjacent to or in contact with the substrate or article to which it is mounted; and "variable stiffness structure" means a construction, part, or combination of parts that causes a non-circular flap to equally deflect under a given load when measured according to the Flap Deflection Test set forth below.

DETAILED DESCRIPTION OF PREFERRED EMBODIMENTS

In practicing the present invention, a centroid-supported flexible flap, secured to a valve seat having a non-circular orifice, is provided with a variable stiffness structure that, despite having flap sections of different lengths from the point of securement, can open essentially equally at any point or segment along the flap perimeter. In known exhalation valves, longer length flaps typically lift more easily from the seal surface since the moment is greater. Because the invention has a variable stiffness structure that imparts a greater stiffness to the flap at radial segments that are longer, an increased force or load is required to open the flap on that radial at the same location. The increased stiffness at that radial counters the greater moment, which enables the flexible flap to equally deflect at different radials extending from the centroid when measured at the point where the various radials intersect with the seal surface. An exhalation valve having this construction may optimize pressure drop and overall valve performance for non-circular exhalation valves. A non-circular valve having this construction also may be beneficially shaped into various configurations where similarly performing cantilevered valves have been limited.

Figure 1:
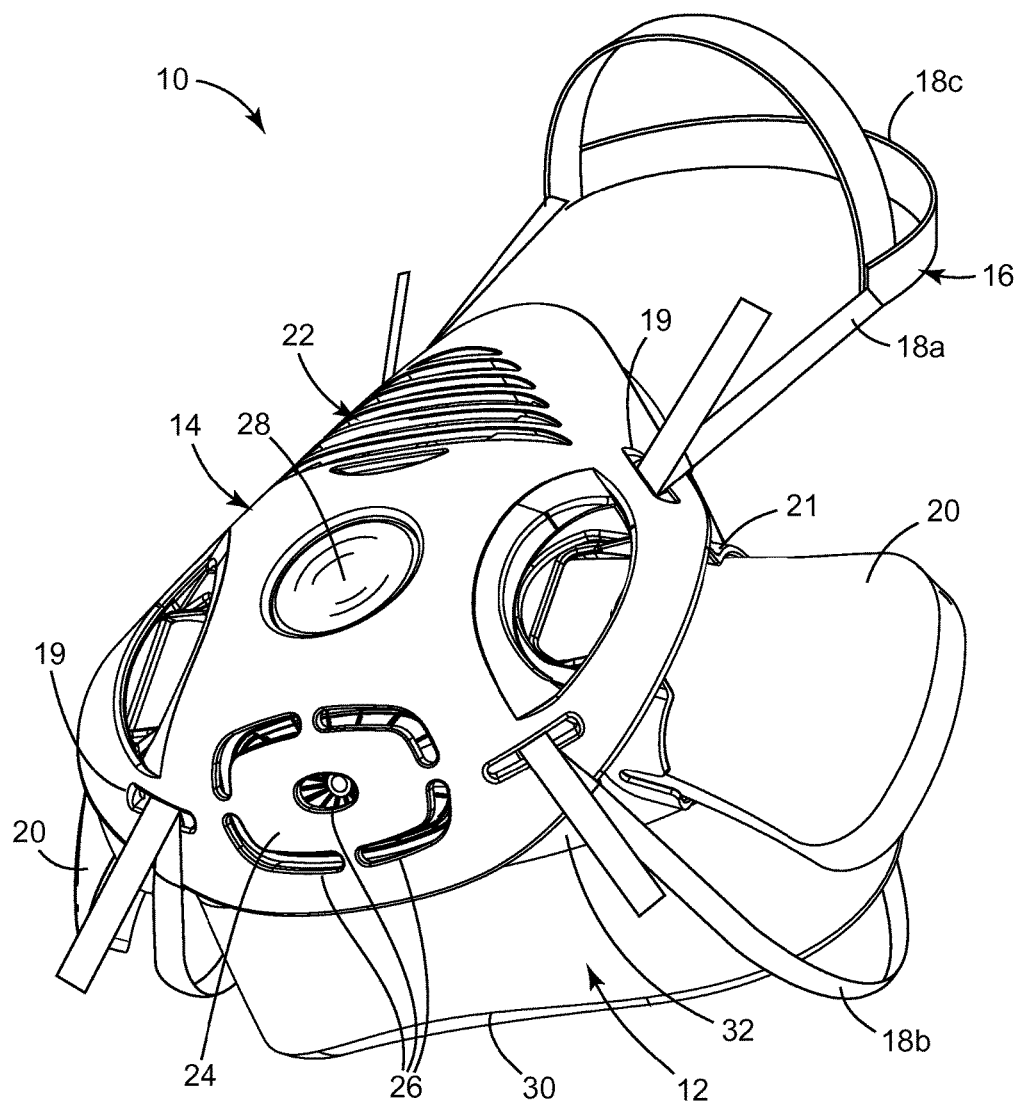
FIG. 1 is a front perspective view of a respirator 10 in accordance with the present invention.

FIG. 1 shows a respirator 10 that has a mask body 12 and a cover plate 14 located on the front of the mask body 12. The respirator 10 also includes a harness 16 that has straps 18a, 18b for supporting the respirator 10 on a wearer's head during use. The upper straps 18a may be attached to a crown member 18c, which rests on the crown of the wearer's head during use. The lower set of straps 18b extends behind the wearer's neck during use and may include a releasable buckle to accommodate ease of attachment and removal. Example of harnesses that may be suitable for use in the present invention are described in U.S. Pat. No. 6,732,733 to Brostrom et al. and U.S. Pat. No. 6,715,490 to Byram. The cover plate 14 may be provided with one or more slots 19 that accommodate the straps 18a, 18b. A pair of filter cartridges 20 is attached to the mask body 12 to provide clean air for the wearer to breathe. The cartridges 20 contain one or more layers of filter media that remove contaminants from the ambient air when the wearer inhales. The filter media may remove particulate contaminants and/or gaseous contaminants, depending on the application. The filter cartridges 20 may be plugged into the cartridge receptacles 21 using the apparatus described in U.S Patent Application 2013/0125896 to Dwyer et al. The respirator 10 also may be provided with a voice transmission apparatus 22 that enables the respirator wearer to more easily communicate with others. An exhalation valve 23 (FIGS. 2-6) may be disposed beneath an exhalation valve cover 24 located on the cover plate 14. The valve cover 24 may have a series of openings 26 in it, which allow exhaled air to pass from the underlying valve into the ambient air space. A negative-pressure check button 28 may be installed centrally on the mask body 12 to allow a respirator wearer to quickly evaluate whether a leak free seal is provided at the mask body face seal 30. To make such an evaluation, a wearer simply pushes the button 28 and inhales. The button push causes the inhalation valve 31 (FIG. 6) to close. If air is detected entering the mask body interior during the attempted inhalation, the face seal is not seated properly on the wearer's face. The respirator may be too large or small, or there may be an obstruction that denies a good face fit. A pressure-check button suitable for such use is described in co-pending U.S. patent application Ser. No. 13/757,373 to Mittelstadt et al. The face seal 30 may be made of a pliant or elastomeric material such as silicone to allow the face seal to fit snugly to various faces. The face seal 30 is secured to a rigid central portion 32 of the mask body 12 to make the resulting product lighter to wear. A mask body 12 that uses such a rigid central portion has been described in U.S. Pat. No. 5,062,421 to Burns and Reischel—see also U.S. Pat. No. 7,650,884 to Flannigan et al.

Figure 2:
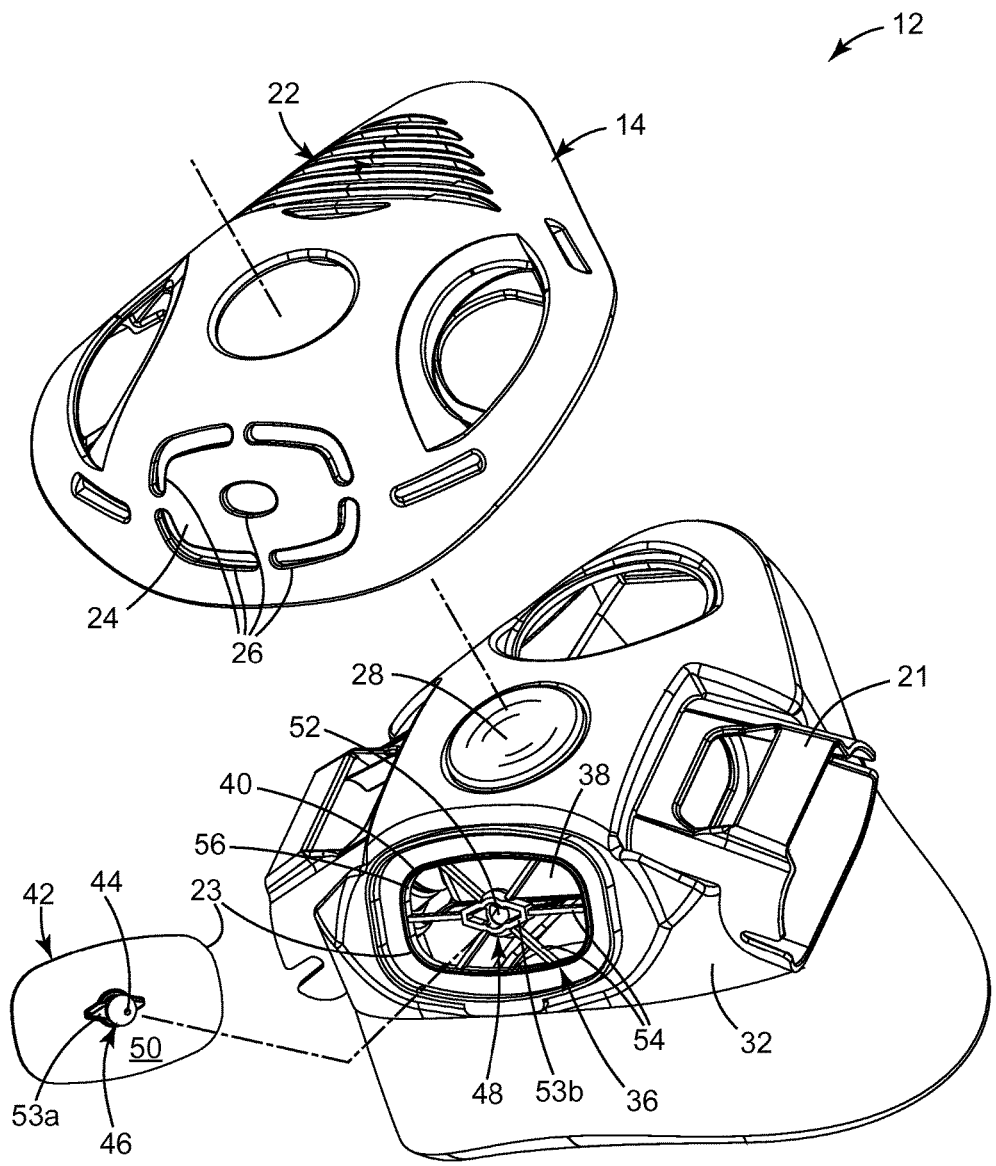
FIG. 2 is a front perspective view of a respirator mask body 12, in accordance with the present invention, showing the valve flexible flap 42 and the cover plate 14 removed therefrom.

FIG. 2 shows the mask body 12 having the cover plate 14 separated therefrom. Located beneath the cover plate 14 is the exhalation valve 23. The exhalation valve 23 has a valve seat 36 that has an orifice 38 and a noncircular seal surface 40 surrounding the orifice 38. The exhalation valve 23 also includes a flexible flap 42 that is secured to the valve seat 36 at a centroid 44 of the flap 42 and that has a variable stiffness structure 46 (FIG. 3) that allows the flexible flap 42 to equally deflect at the valve seat seal surface 40 in response to a force exerted by a wearer's exhaled air. The flexible flap 42 also has a first alignment element 46, and the valve seat 36 has a second alignment element 48 that mates with the first alignment element 46. The first and second alignment elements 46 and 48 enable the flexible flap 42 to be properly oriented on the valve seat 36. Establishing proper orientation is particularly important in a non-circular flap since a slight rotation of flap 42 about the centroid 44 may cause the underside 50 of flap 42 to reside out of contact with the seal surface 40. Button valves, for example, only need to be aligned centrally because valve flap rotation is not an issue. The first and second alignment elements 46 and 48 accordingly not only provide for alignment of the flap centroid 44 with the valve seat centroid 52 but they also preclude rotation of the flap 42 about the centroid 52 in the flap plane. To do so, the first alignment element 46 includes one or more rotation-prevention elements 53a that mate with a similarly sized rotation-prevention elements 53b in the second alignment element 48. The valve seat 36 also can be provided with one or more joists 54 that extend radially from the second alignment element 48 to the orifice inner edge 56 (FIG. 2). The joists 54 support the second alignment element 48 within the valve orifice 38 at its proper location.

Figure 3:
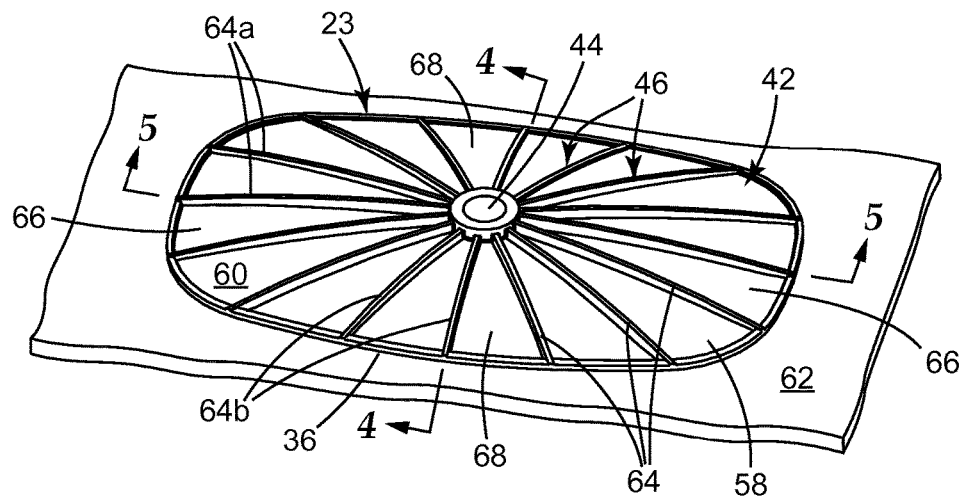
FIG. 3 is a front perspective view of the exhalation valve 23.

FIG. 3 shows the exhalation valve 23 with the flexible flap 42 resting on the valve seat 36 (FIGS. 4 and 5) in the closed position. The flap 42 typically is biased toward the valve seat 36 when it its closed position. The bias preferably is fashioned to be "slight", that is, the bias is fashioned to keep the flap 42 in a closed position under minimal force regardless of valve orientation when airflow forces are not being exerted on the flap 42. A slight bias may be achieved by constructing the variable stiffness structure 46 to cause the flap 42 to remain closed along all points around the flap perimeter 58 when inverted and exposed only to gravity. The flexible flap 42 also is adapted to equally deflect in response to an exhalation pressure. The variable stiffness structure 46 enables any segment of the flap perimeter 58 to have an essentially equal chance of being lifted from the seal surface 40 (FIGS. 2, 4, and 5) during an exhalation. The illustrated flap 42 and the underlying seal surface 40 both have an oblong shape when viewed through a plane projected onto the outer major surface 60 of the flexible flap 42. Essentially all other non-circular shapes are contemplated within this invention. The flap 42 and seal surface 40 do not necessarily have to have the same shape, although such is typically preferred for better performance. The flap 42 and seal surface 40 may have, for example, a rectangular, square, triangular, elliptical, hexagonal, octagonal, irregular, or other shape. The valve seat 36 is secured to a substrate material 62 when in use. The substrate material 62 may be one or more of the materials that comprises the mask body 12 (FIG. 1). If the valve is attached to a filtering face mask—see, for example, U.S. Pat. No. 7,131,442 to Kronzer et al. and U.S. Pat. No. 6,923,182 to Angadjivand et al—the valve seat may be secured to the nonwoven fibrous materials of the mask body filtering structure. If the mask body is one that contains filter cartridges or insert molded filter elements—see, for example, U.S. Pat. No. 6,883,518 to Mittelstadt et al. and U.S. Pat. No. 4,790,306 to Braun—the valve seat may be molded into the mask body or it may be secured thereto. The valve seat also can be secured to a frame that is supported by the mask body support structure—see, for example, U.S. Patent Application 2009/0078264 to Martin et al. The variable stiffness structure 46 may include a plurality of ribs 64 that extend radially from the centroid 44. The adjacent ribs may be separated from each other at an angle of about 10 to 45 degrees, more typically about 15 to 30 degrees. The longer ribs 64a that extend from the flap centroid 44 to the longer ends 66 are configured to be stiffer than the shorter ribs 64b that extend from the flap centroid 44 to the shorter ends 68 of the flap 42. The different degrees of stiffness may achieved by making the stiffer ribs 64a taller or wider than the less stiff ribs 64b. Thus, the cross section of the stiffer ribs 64a may be greater than the cross section of the less stiff ribs 64b. The difference in cross-sectional area may be about 10 to 50%. Alternatively, the stiffer ribs 64a may be made from a stiffer material than the less stiff ribs 64b while having a similar cross section. Another way to provide a variable stiffness structure is to make the flap 42 thicker in the sections that have the greater length or moment. Flaps that have ribs and non-uniform thicknesses are described in U.S. Pat. No. 6,883,518 to Mittelstadt et al. The flexible flap may be provided with a non-uniform thickness where the longer flap sections have a greater thickness than the shorter flap sections. A flap having a variable thicknesses can be provided by ablating different portions of the flap using, for example, a laser—see U.S Patent Applications Nos. 2012/0167890 and 2012/0168658 to Insley et al. The flexible flap also may be precurved, which precurvature becomes flattened when the flap is secured to the valve seat—see the '518 patent to Mittelstadt et al.

Figure 4:
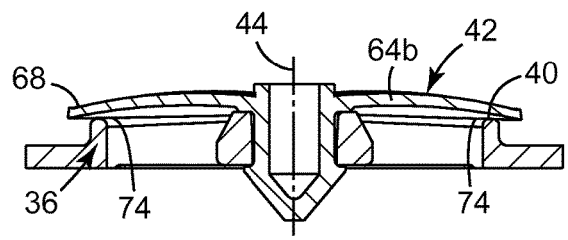
FIG. 4 is a cross-section of the exhalation valve 23 taken along lines 4-4 of FIG. 3.
Figure 5:
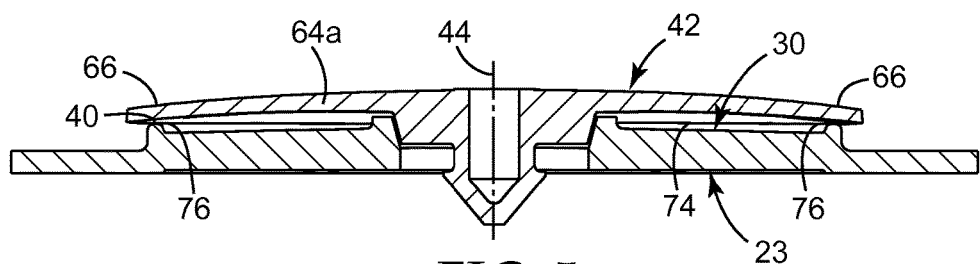
FIG. 5 is a cross-section of the exhalation valve 23 taken along lines 5-5 of FIG. 3.

FIGS. 4 and 5 show how the longer ribs 64a have a greater height than the shorter ribs 64b. The increase in rib height with a similar width creates a larger cross section and thereby increases the rib stiffness. The stiffer rib 64a keeps the free end 66 of the flap 42 biased toward the seal surface 40 so that it remains closed despite the orientation of the valve 23. The shorter free end of 68 of flap 42 therefore has an equal chance of being deflected when compared to the longer free end 66. The flap deflection ration (FDR) for flexible flaps, used in connection with the present invention, is less than 2, preferably less than 1.5, and more preferably less than 1.4 when tested according to the Flap Deflection Test set forth below. The FDR preferably is as close to 1 as possible. FDRs less than 1.3, 1.2 and 1.1 also can be achieved. Typically any point measured along the flap perimeter 58 at any radial extending from the centroid using the Flap Deflection Test exhibits no more than 10 millinewtons (mN) load, preferably no more than 5 mN, to deflect the flap 1 millimeter (mm). Each point along the flap perimeter measured for load to deflect the flap this 1 mm distance preferably does not differ from any other point so measured by more than 100%, more preferably by more than 50%, and still more preferably by more than 25%.

Figure 6:
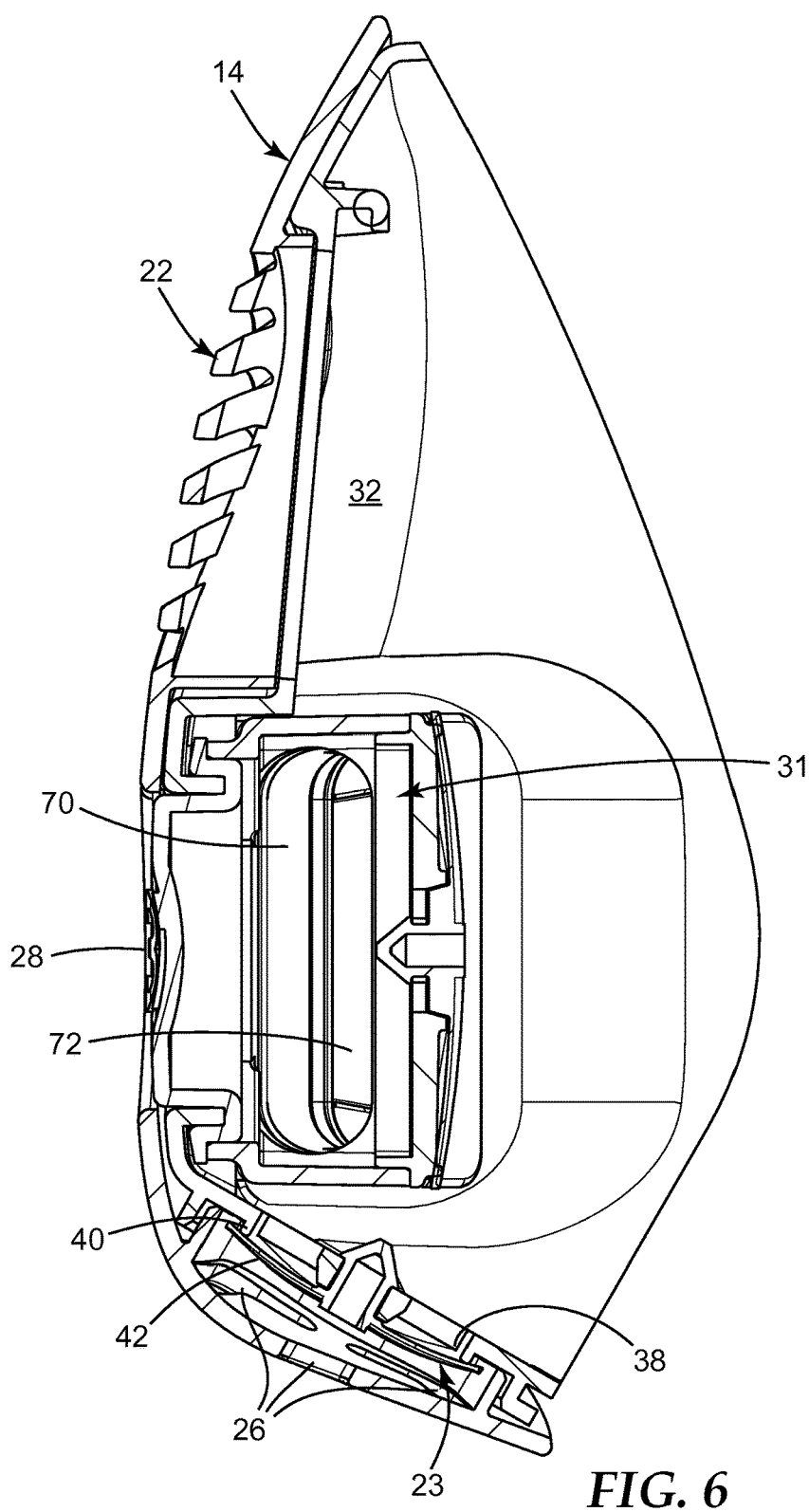
FIG. 6 is a vertically bisecting cross-sectional view taken through the central portion 32 of the mask body 12.

FIG. 6 shows the central portion 32 of the mask body 12 (FIG. 2) in cross section. When the respirator 10 (FIG. 1) is in use, the mask body 12 separates the interior gas space from the exterior gas space. Clean air that enters the interior gas space through port 70 passes into a central plenum 72 before it passes through inhalation valve 31 where it can then be inhaled by the respirator wearer. The clean air is created by first passing through a filter cartridge 20 (FIG. 1). The cartridge 20 is plugged into receptacle 21 (FIG. 2) when the respirator is being used. A mask body that has this configuration is described in U.S. patent application Ser. No. 13/757,068 to Dwyer et al. Air that is exhaled by the wearer passes from the interior gas space to the exterior gas space through the exhalation valve 23. The exhaled air stream or air pressure lifts a free end of the flexible flap 42 from the seal surface 40 to allow air to pass through valve orifice 38 and openings 26 in cover plate 14. In lieu of a cover plate 14, a valve cover may be used to protect the valve and to direct exhaled air downwardly. An example of a valve cover is shown in U.S. patent Des. 347,299 to Japuntich et al.

EXAMPLES

Flap Deflection Test

This test measures the load or force needed to lift the flexible flap from the valve seat seal surface 1 mm in height.

To carry out this test, the exhalation valve is first positioned in a test apparatus that is properly calibrated. Three-Zaber motion linear translation motion stages (model T-LSR 150 are used for 3D sample positioning. They are assembled such that the clamping fixture with the attached sample may be translated in three dimensions for sample positioning and loading via manually operated pots on each stage. The clamping fixture is fashioned to hold the valve seat. A Transducer Techniques load cell (model GS0-10) is positioned below sample in the area of interest with a static fixture and with an 0.5 mm attached flat punch. The flat punch has a diameter of 0.5 mm at the tip with a 1 mm diameter shank of length 16 mm which is attached to a threaded stud which in turn threads into the load cell. The length of the flat punch is 1.25 inches. A Universal Serial Bus (USB) Dinolite™ microscope is set 2.75 inches from the probe/sample for a side view of the punch lifting the flap. The load cell is wired to a 10 volt DC supply via a Transducer Techniques model TMO-1 conditioner where the gain is set to the maximum value. The load cell is attached to a static stand with the punch facing upward towards area of interest. The load cell is tuned using a pot on the TMO-1 conditioner. The load cell and the USB microscope are interfaced to a computer via a Measurement Computing FS1408 USB data acquisition board and an associated Tracer DAQ and Instacal software. The data acquisition board is selected and tested with the Instacal™ software. The load cell is calibrated with gram weights, then a linear fit of the force (mN) vs. millivolt output is calculated. The sample is clamped to the motion stage fixture with flap installed on the valve seat. The punch is located underneath the regions to be tested via the motion stage. The distance measurement is enabled by placing a graduated ruler next to where the flap is to be lifted. The resultant image is saved for 0.5 mm gradations.

Once the test sample is properly positioned in the device, the following steps are carried out to measure the load needed to lift the flexible flap from the seal surface:

1. The punch is positioned beneath the flexible flap at the location where the flap meets the seal surface. The punch is almost touching the valve. The data acquisition for the load channel is initiated for Tracerdaq™ software. A sample rate of 100 samples/sec and 3 minute sample length is used to take the data.

2. Immediately after the load channel begins to accumulate data, the operator switches to the video screen to see the probe in near contact with sample. Video recording is initiated.

3. Using z-stage control, the sample is lowered onto probe while the video shows the valve flap lifting from base due to engagement with the probe.

4. At a lift value of approximately 1 mm, the dwell controller maintains the probe in place for a 2-3 second time period.

5. After the dwell segment is completed, the load is removed from flap using the z-stage controller.

6. A dwell at zero load is then held for 5 seconds.

7. Steps 3-6 are repeated twice more.

8. Load vs. time is saved in Tracerdaq™ software; the video is saved in the Dinolite software.

9. The video is reviewed to frame the maximum lift during the test. Then the 1 mm lift distance is measured and verified using a calibration from the graduated ruler.

The output from the system is in millivolts. The linear fit is used to determine the load, which is then reported in milliNewtons (mN). The load at a 1 mm deflation is measured at two locations. Location 1 is the point where the shortest radial extending from the centroid intersects with the inside surface of the valve orifice, and location 2 is the point where the longest radial intersects with the inside surface of the valve orifice. Location 1 is identified in FIG. 4 by numeral 74, and location 2 is identified in FIG. 5 by numeral 76.

Example E1

An exhalation valve that resembled the valve shown in FIGS. 2-6 was constructed. The flexible flap was molded using a Wacker Elastosil 3001-60 silicone rubber. The valve seat and its sealing surface were made from a stereolithography (SLA) process using an Accura™ 60 rapid prototype material. The flexible flap had a long axis length of 41 millimeters (mm) (20.5 mm from the centroid) and had a short axis length of 25 mm (12.5 mm from the centroid). The flexible flap was designed to stay shut under a gravity load at any orientation. The ribs were located oriented as shown in FIG. 3. The ribs extended radially from the centroid such that adjacent ribs were spaced from each other at about 24 degrees. The angular spacing was the same for each of the ribs. The continuous flap sheet that was joined to the ribs had a thickness of about 0.28 mm. In an earlier construction that lacked ribs attached to this flap sheet, the flap was found to not stay shut in all orientations under a gravity load. The cross-sectional area of the ribs varied. The ribs at the long axis had a maximum cross-sectional area of about 0.25 mm². The ribs at the short axis had a maximum cross-sectional area of about 0.13 mm². Ribs that had such a cross-sectional area were found to buckle when the flap was exposed to a force that caused the flap to bend. The length of the longest rib was 18.5 mm. The length of the shortest rib was 10.2 mm. The rib height at the centroid of the longest rib was 0.82 mm. The rib height at the centroid of the shortest rib was 0.42 mm. The tallest rib tapers to approximately a 0.4 mm height at the perimeter. The rib width was 0.31 mm and was the same for all ribs. All the ribs intersect a boss located at the flap centroid. The boss had a 4.5 mm diameter. An alignment element is symmetrical about the centroid and is 3 mm wide and 10.2 mm long. The alignment element tapers from the flap membrane to a plane that has a maximum distance of 2.8 mm from the flap.

The valve seat was produced to have the configuration shown in FIGS. 2, 4, and 5. The valve seat was created by rapid prototyping.

The flexible flap was joined to the valve seat by pushing the center boss and alignment feature into a corresponding mating feature on the valve seat. The mating feature has a hole that accepts the boss/alignment feature and holds the valve onto the valve seat The resulting exhalation valve was tested according to the Flexible Flap Test, and the results are set forth below in Table 1.

TABLE 1

| E1 Results | | | |
|---|---|---|---|
| Deflection (mm) | Location 1 Force (mN) | Location 2 Force (mN) | FDR |
| 1 | 2.45 | 1.74 | 1.40 |

Table 1 shows the FDR for E1, which was 1.40 (2.45/1.74). This data show that the resulting exhalation valve has a FDR within the scope of the present invention. The flexible flap therefore can equally deflect, allowing any segment of the flap perimeter to be lifted from the valve seat during an exhalation.

Deflection/Force Simulation

Finite element analysis software can be used to compare the deflection characteristics of a flexible flap that has a variable stiffness structure to an equivalent flap that lacks such a structure. A computer model of the valve system consists of a mesh of finite elements that represents the flap geometry. Finite elements are small domains of the entire structure. The governing differential equations are numerically calculated across these elements. Each element is bounded by nodes with straight lines between them. Nodes may be a part of a number of neighboring finite elements. All of the elements connected together represent a mesh. This mesh closely approximates the geometry of the structure you are analyzing.

The flexible flaps are thin walled structures that can use shell finite elements to approximate the flap thickness. Shell elements are typically triangular flat elements that have 3 nodes. A shell model has the appropriate thickness applied to the elements as an attribute. The thickness is then accounted for in the computations. If desired, three-dimensional elements can be used to model the thickness also. These 3D elements typically have four faces and three nodes.

To reduce the model size, symmetry can be used. Appropriate boundary conditions need to be applied to the model across planes of symmetry. Nodes that lie on this plane are constrained to allow rotation only within that plane. They are also constrained to ensure there is no deflection out of the plane.

Since the flap is constrained at the support feature at the centroid, the model can be further simplified if desired. For the simulation, the nodes on the seal membrane and the ribs can be fixed at the intersection with the center support instead of modeling the entire support.

The shell mesh needs to be created with a sufficient number of elements to accurately model the flap geometry and the contact to the seal surface. The seal surface should be modeled with rigid contact elements. To preload the flap, the seal surface elements are raised into the flap mesh, which creates the preload.

A representative elastic modulus and a poisson's ratio are applied to the model. The model of the flap without a gravity load is now complete.

For the simulation, one of the nodes at the desired location is raised off of the rigid elements, which represent the sealing surface. The nodes are raised in small increments until the final deflection is reached. For this simulation, the deflection is limited so the effect of the stiffness of the neighboring region does not dominate the results. This technique can replicate the Flap Deflection Test. The results from the analysis are the force at a given deflection at the noted location.

Simulated Exhalation Valve—Example SE1

The exhalation valve produced according to this example was a valve that had the same flexible flap as example E1, that is, it was a computer simulation of the E1 valve having the same flexible flap. The finite element analysis software used in this example was ABAQUS®. The simulated example used a modulus of 350 pounds per square inch (psi) and a Poisson's ratio of 0.5 to represent the 3001-60 silicone material. An analysis was run at each of the two locations specified in the Flap Deflection Test (Location 1 and Location 2). At each location, the flap was raised off the contact elements, representing the seal surface at one location. The maximum deflection used was 1 mm. The deflection was applied in ten increments until the flap was opened to the maximum deflection value. At each increment, the reaction load was calculated by the software.

To maximize the flap efficiency, at a defined opening around the perimeter, the loads should be "equivalent". Stated differently, the flap deflection should be the same at a given load. To determine this, the FDR is calculated from the output of the analysis between locations 1 and 2 at the valve seal surface. The FDR between the longest and the shortest radials was used as a representative measure of this equivalency. Table 2 shows the resultant force and FDR for each deflection increment for example SE1.

TABLE 2

| | SE1 Results | | |
|---|---|---|---|
| Displacement (mm) | Location 1 Force (mN) | Location 2 Force (mN) | FDR Ratio |
| 0.2 | 0.260 | 0.198 | 1.30 |
| 0.3 | 0.334 | 0.262 | 1.27 |
| 0.4 | 0.387 | 0.308 | 1.26 |
| 0.5 | 0.439 | 0.349 | 1.26 |
| 0.6 | 0.484 | 0.387 | 1.25 |
| 0.675 | 0.525 | 0.421 | 1.25 |
| 0.75 | 0.566 | 0.453 | 1.24 |
| 0.85 | 0.594 | 0.482 | 1.23 |
| 0.95 | 0.624 | 0.508 | 1.23 |
| 1 | 0.653 | 0.532 | 1.23 |
| | | AVG | 1.25 |

At 1 mm deflection, the SE1 FDR is 1.23 which shows good correlation to the E1 FDR of 1.4 considering modeling and test variability.

Simulation Comparison Example—SCE1

SCE1 is a simulation of the test run in E1, using the same flap as E1, with exception of having the ribs removed. The same simulation approach was replicated from SE1, but the ribs were removed from the mesh. Table 3 shows the resultant force and FDR for each deflection increment.

TABLE 3

| | SCE1 Results | | |
|---|---|---|---|
| Displacement (mm) | Location 1 Force (mN) | Location 2 Force (mN) | FDR Ratio |
| 0.2 | .0158 | 0.133 | 8.41 |
| 0.3 | .0309 | 0.163 | 5.25 |
| 0.4 | .0452 | 0.188 | 4.15 |
| 0.5 | .0589 | 0.210 | 3.56 |
| 0.6 | .0719 | 0.229 | 3.18 |
| 0.675 | .0844 | 0.246 | 2.92 |
| 0.75 | .0964 | 0.263 | 2.73 |
| 0.85 | 0.108 | 0.278 | 2.58 |

TABLE 3-continued

| | SCE1 Results | | |
|---|---|---|---|
| Displacement (mm) | Location 1 Force (mN) | Location 2 Force (mN) | FDR Ratio |
| 0.95 | 0.119 | 0.294 | 2.46 |
| 1 | 0.130 | 0.306 | 2.34 |
| | | AVG | 3.76 |

Table 2 and Table 3 show the results for SE1 and SCE1 respectively. As expected, the non-ribbed version had lower loads. This was expected because the membrane thickness was maintained at 0.28 mm. This flap thickness, however, was not adequate to hold the valve shut in all orientations under gravity.

Both tables show the FDR at locations 1 and 2 for each case. A fully optimized system would have a ratio of 1. SE1 has an average ratio of 1.25 when deflected at increments between 0.2 mm to 1 mm. The "equivalent" stiffness example (SCE1) without the ribs had a much higher average ratio of 3.76. At 1 mm deflections, the FDRs were 1.23 and 2.34 respectively.

Simulated Exhalation Valve—Example SE2

Another exhalation valve with a lower aspect ratio was analyzed. The flexible flap had a long axis length of 35.5 millimeters (mm) (17.75 mm from the centroid) and had a short axis length of 32 mm (16 mm from the centroid). The flexible flap was designed to stay shut under a gravity load at any orientation. The ribs extended radially from the centroid such that adjacent ribs were spaced from each other at about 24 degrees. The angular spacing was the same for each of the ribs. The continuous flap sheet that was joined to the ribs had a thickness of about 0.28 mm. The cross-sectional area of the ribs varied. The ribs at the long axis had a maximum cross-sectional area of about 0.23 mm$^2$. The ribs at the short axis had a maximum cross-sectional area of about 0.19 mm$^2$. Ribs that had such a cross-sectional area were found to buckle when the flap was exposed to a force that caused the flap to bend. The length of the longest rib was 16.9 mm. The length of the shortest rib was 14.0 mm. The rib height at the centroid of the longest rib was 0.77 mm. The rib height at the centroid of the shortest rib was 0.68 mm. The tallest rib tapers to approximately a 0.4 mm height at the perimeter. The shortest rib tapers to approximately a 0.25 mm height at the perimeter. The rib width was 0.31 mm and was the same for all ribs. The boss and alignment feature were the same as described in SE1.

The finite element analysis software used in this example was ABAQUS®. The simulated example used a modulus of 350 pounds per square inch (psi) and a Poisson's ratio of 0.5 to represent the 3001-60 silicone material. An analysis was run at each of the two locations specified in the Flap Deflection Test (Location 1 and Location 2). At each location, the flap was raised off the contact elements, representing the seal surface at one location. The maximum deflection used was 1 mm. The deflection was applied in ten increments until the flap was opened to the maximum deflection value. At each increment, the reaction load was calculated by the software.

The results for the simulation are shown in table 4

TABLE 4

| | SE2 Results | | |
|---|---|---|---|
| Displacement (mm) | Location 1 Force (mN) | Location 2 Force (mN) | FDR |
| 0.2 | 0.244 | 0.328 | 1.35 |
| 0.3 | 0.305 | 0.411 | 1.35 |
| 0.4 | 0.347 | 0.471 | 1.36 |
| 0.5 | 0.382 | 0.519 | 1.36 |
| 0.6 | 0.418 | 0.557 | 1.33 |
| 0.675 | 0.448 | 0.589 | 1.31 |
| 0.75 | 0.486 | 0.618 | 1.30 |
| 0.85 | 0.502 | 0.645 | 1.29 |
| 0.95 | 0.526 | 0.672 | 1.28 |
| 1 | 0.549 | 0.698 | 1.27 |
| | | AVG | 1.32 |

Simulation Comparison Example—SCE2

For SCE2 the same simulation approach was replicated from SE2, but the ribs were removed from the mesh. Table 5 shows the resultant force and FDR for each deflection increment.

TABLE 5

| | SCE2 Results | | |
|---|---|---|---|
| Displacement (mm) | Location 1 Force (mN) | Location 2 Force (mN) | FDR Ratio |
| 0.2 | 0.126 | 0.242 | 1.92 |
| 0.3 | 0.166 | 0.302 | 1.82 |
| 0.4 | 0.197 | 0.343 | 1.74 |
| 0.5 | 0.218 | 0.376 | 1.73 |
| 0.6 | 0.235 | 0.402 | 1.71 |
| 0.675 | 0.251 | 0.424 | 1.69 |
| 0.75 | 0.267 | 0.444 | 1.66 |
| 0.85 | 0.282 | 0.463 | 1.64 |
| 0.95 | 0.297 | 0.481 | 1.62 |
| 1 | 0.312 | 0.496 | 1.59 |
| | | AVG | 1.71 |

Table 4 and Table 5 show the results for SE2 and SCE2 respectively. Both tables show the FDR at locations 1 and 2 for each case. SE2 has an average ratio of 1.32 when deflected at increments between 0.2 mm to 1 mm. The "equivalent" stiffness example (SCE2) without the ribs had a higher ratio of 1.71. At 1 mm deflection, the FDR's were 1.32 and 1.51 respectively.

The FDR's were closer due to an aspect ratio's approaching 1. The advantage of a variable stiffness flap decreases as the shortest length radial and the longest length radial become similar. However, there is still an advantage as long as the radials are of difference lengths.

The variable stiffness valves, SE1 and SE2, had "equivalent load" for equal deflections when comparing the perimeter location at the longest distance from the centroid to the location at the shortest distance to the centroid This results in the flap lifting open around the entire periphery under a given exhalation pressure. With more flap perimeter lifting a greater distance from the seal surface, the pressure drop decreases across the valve orifice, which increases user comfort by reducing the exhalation pressure at a given flow rate.

This invention may take on various modifications and alterations without departing from its spirit and scope. Accordingly, this invention is not limited to the above-described but is to be controlled by the limitations set forth in the following claims and any equivalents thereof.

This invention also may be suitably practiced in the absence of any element not specifically disclosed herein.

All patents and patent applications cited above, including those in the Background section, are incorporated by reference into this document in total. To the extent there is a conflict or discrepancy between the disclosure in such incorporated document and the above specification, the above specification will control.

What is claimed is:

1. An exhalation valve that comprises:
   a valve seat that has an orifice and that has a noncircular seal surface surrounding the orifice; and
   a noncircular flexible flap that is secured to the valve seat at a centroid of the flexible flap and that has a variable stiffness structure.

2. The exhalation valve of claim 1, wherein the flexible flap has a first alignment element.

3. The exhalation valve of claim 2, wherein the valve seat has a second alignment element that mates with the first alignment element.

4. The exhalation valve of claim 3, wherein the first and second alignment elements preclude rotation of the flexible flap about a centroid of the orifice in the flap plane.

5. The exhalation valve of claim 4, wherein the first alignment element includes a rotation-prevention element(s) that mate with a similarly sized rotation-prevention element(s) in the second alignment element.

6. The exhalation valve of claim 3, wherein the valve seat has one or more joists that extend radially from the second alignment element to an inner edge of the orifice.

7. The exhalation valve of claim 6, wherein the joists support the second alignment element within the valve orifice at a centroid of the orifice.

8. The exhalation valve of claim 6, wherein the flap is biased toward the valve seat when it its closed position.

9. The exhalation valve of claim 1, wherein the variable stiffness structure includes a plurality of ribs that extend radially from the centroid of the flexible flap.

10. The exhalation valve of claim 9, wherein at least some of the plurality of ribs have different lengths, and wherein longer ribs are configured to be stiffer than shorter ribs.

11. The exhalation valve of claim 1, wherein no more than 5 mN of force is needed to lift the flexible flap 1 mm from the noncircular seal surface at any point along the flap perimeter when measured according to the Flexible Flap Test.

12. A respirator that comprises:
    a harness; and
    a mask body that comprises an exhalation valve that includes:
      a valve seat that has an orifice and that has a noncircular seal surface surrounding the orifice; and
      a noncircular flexible flap that is secured to the valve seat at a centroid of the flexible flap and that has a variable stiffness structure.

13. The respirator of claim 12, wherein the flexible flap has a first alignment element.

14. The respirator of claim 13, wherein the valve seat has a second alignment element that mates with the first alignment element.

15. The respirator of claim 14, wherein the first and second alignment elements preclude rotation of the flexible flap about a centroid of the orifice in the flap plane.

16. The respirator of claim 15, wherein the first alignment element includes a rotation-prevention element(s) that mate with a similarly sized rotation-prevention element(s) in the second alignment element.

17. The respirator of claim 14, wherein the valve seat has one or more joists that extend radially from the second alignment element to an inner edge of the orifice.

18. The respirator of claim 17, wherein the joists support the second alignment element within the valve orifice at a centroid of the orifice.

* * * * *